(12) United States Patent
Rosen

(10) Patent No.: US 7,189,225 B2
(45) Date of Patent: Mar. 13, 2007

(54) DEVICE FOR CONJUNCTIVAL/SCLERAL COMPRESSION TO CONSTRICT SUPERFICIAL BLOOD FLOW AND METHOD OF USE

(76) Inventor: Robert S. Rosen, 950 Valley Rd., Solana Beach, CA (US) 92075

( * ) Notice: Subject to any disclaimer, the term of this patent is extended or adjusted under 35 U.S.C. 154(b) by 159 days.

(21) Appl. No.: 11/124,948

(22) Filed: May 9, 2005

(65) Prior Publication Data

US 2006/0253110 A1 Nov. 9, 2006

(51) Int. Cl.
*A61B 18/18* (2006.01)
*A61F 19/00* (2006.01)
(52) U.S. Cl. .............................. 606/6; 606/4; 606/166
(58) Field of Classification Search ............... 606/4–6, 606/166
See application file for complete search history.

(56) References Cited

U.S. PATENT DOCUMENTS

| 5,336,215 | A | * | 8/1994 | Hsueh et al. | 606/4 |
| 5,549,632 | A | * | 8/1996 | Lai | 606/5 |
| 5,616,139 | A | * | 4/1997 | Okamoto | 606/4 |
| 6,254,595 | B1 | * | 7/2001 | Juhasz et al. | 606/5 |
| 6,373,571 | B1 | * | 4/2002 | Juhasz et al. | 356/399 |
| 6,569,153 | B1 | * | 5/2003 | LaHaye | 606/4 |
| 7,018,376 | B2 | * | 3/2006 | Webb et al. | 606/4 |
| 7,087,050 | B2 | * | 8/2006 | LaHaye | 606/4 |

* cited by examiner

*Primary Examiner*—A. Farah
(74) *Attorney, Agent, or Firm*—Caesar, Rivise, Bernstein, Cohen & Pokotilow, Ltd.

(57) ABSTRACT

A device and method for applying external compression to the eye of a living being to reduce bleeding when operating on the surface of the eye. The device includes a peripheral wall and a pair of spaced apart, pressure applying rings. One of the rings applies pressure to a first peripheral portion of the eye closely adjacent and surrounding the cornea, while the other ring applies pressure to a second peripheral portion of the eye remote from the cornea. The wall includes at least one window to provide access to a portion of the surface of the eye to enable a laser beam to be extended therethrough to operate on the surface of the eye between the two peripheral portions of the eye.

12 Claims, 1 Drawing Sheet

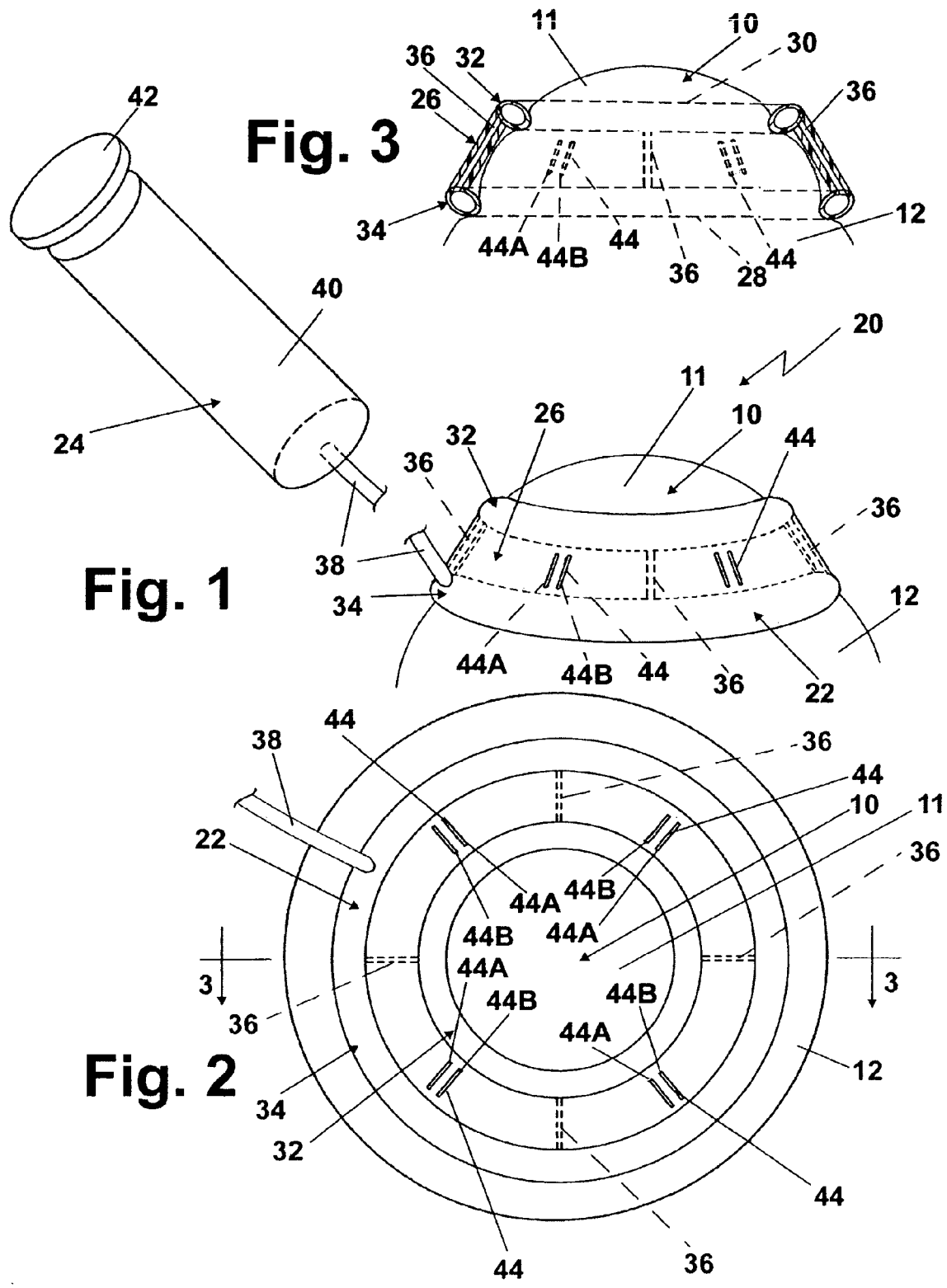

DEVICE FOR CONJUNCTIVAL/SCLERAL COMPRESSION TO CONSTRICT SUPERFICIAL BLOOD FLOW AND METHOD OF USE

FIELD OF THE INVENTION

This invention relates generally devices for surgery on the eye of a living being and more particularly to devices and methods of use for applying external compression to portions of the eye to reduce bleeding when operating on the surface of the eye.

BACKGROUND OF THE INVENTION

The external part of the eye is surrounded by the conjunctiva (a highly vascular membrane) and the sclera (a less vascular structure that gives the eye its shape and acts as a supporting structure). While performing various types of surgery starting at the surface, the eye has a tendency to bleed. In order to perform surgery for glaucoma, presbyopia, retinal problems, etc., it is necessary to control the bleeding. In addition, for cosmetic reasons it is desirable to have the eye look as white and quiet as possible after the surgery has been completed.

A need exists for a device to achieve those ends. The subject invention addresses and achieves those ends.

SUMMARY OF THE INVENTION

A device and method of use for applying external compression to the eye of a living being to reduce bleeding when operating on the surface of the eye. The device comprises a peripheral wall having an open upper end and an open lower end, a first ring member (e.g., an inflatable ring), a second ring member (e.g., an inflatable ring) and fluid pressure means (e.g., a spring biased syringe) for causing at least portions of those rings to apply pressure to the first and second portions of the eye.

The wall of the device includes at least one window, e.g., plural pairs of narrow slits, to enable a laser beam or other instrumentality to be extended therethrough to operate on the surface of the eye between the two peripheral portions of the eye.

DESCRIPTION OF THE DRAWING

FIG. 1 is an isometric view of one exemplary device constructed in accordance with this invention shown in use on the eye of a living being;

FIG. 2 is a top plan view of a portion of the device shown in FIG. 1; and FIG. 3 is a vertical sectional view taken along line 3—3 of FIG. 2.

DETAILED DESCRIPTION OF THE PREFERRED EMBODIMENT

Referring now to the various figures of the drawing wherein like reference characters refer to like parts, there is shown at 20 in FIG. 1 a device arranged to be disposed on the eye 10 of a living being, centered over the cornea 11 for applying fluid pressure onto underlying peripheral portions of the eye to fixate the eye and compress the external blood vessels. In particular, as will be described hereinafter, the use of the device 20 produces an avascular field (like using a tourniquet when performing surgery on an extremity like a hand or foot) to effect the compression of the eye's underlying external blood vessels to minimize or otherwise reduce bleeding. As will also be seen and described, the device 20 includes windows, e.g., apertures, enabling a laser beam or mechanical instrumentality to be extended therethrough to operate on the surface of the eye, without adversely affecting the compression provided by the device. The fluid pressure to compress the underlying portions is created by a spring-biased syringe.

To that end as can best be seen in FIG. 1 the device 20 basically comprises a pressure applying subassembly 22 and an actuating subassembly 24. The pressure applying assembly is in the form of a peripheral wall 26, e.g., a frustoconical cylinder, which tapers upward from an open lower end portion 28 to an open upper end portion 30. A first pressure applying ring 32 is located immediately adjacent the open upper end portion 30 and extends about the inner periphery thereof. In a similar manner a second pressure applying ring 34 is located immediately adjacent the open lower end portion 28 and extends about the inner periphery thereof. and a lower end portion. In the exemplary embodiment shown herein, each ring is a hollow inflatable member formed of a soft material, e.g., silicone rubber, so as not to injury the eye when it engages the eye as will be described later. Each ring is arranged to be inflated by an inflation fluid, e.g., air, etc., introduced by the actuating subassembly 24. The details of the actuating subassembly 24 will be described later.

The interior of both of the rings 32 and 34 are in fluid communication with each other via plural passageways 36 extending through the wall 26 of the pressure applying subassembly 22. As best seen in FIG. 2, the passageways are equidistantly spaced around the wall 26. The actuating fluid is arranged to be introduced into the communicating inflatable rings 32 and 34 via a conduit or tube 38 (FIGS. 1 and 2). In the exemplary embodiment shown the tube 38 is connected and in fluid communication with the interior of the lower ring 34. This is merely exemplary. Thus, the tube 38 can be connected to the upper ring 32 or directly to any of the passageways 36 since all are in fluid communication with one another. The tube 38 serves as the outlet of the actuating subassembly 24. In the exemplary embodiment shown the actuating subassembly basically comprises a syringe-like member 40 which includes a piston (not shown) that is biased by a spring (not shown). A reservoir of inflating fluid e.g., air, is located within the member 40 and is arranged to be expelled through the tube 38 upon movement of the piston. The piston is biased by the spring. The syringe includes a top button or cap 42, which when depressed causes the spring to force the piston toward the tube 38, thereby driving the fluid out of the member 40 and into the rings 32 and 34 via the communicating passageways 36.

The inflation of those rings applies a compressive force to the underlying portions of the eye as will be described later. This action reduces or minimizes bleeding.

Once the device 20 is in place on the eye the surgical or other procedure may proceed. In order to provide access to the portion of the surface of the eye upon which the procedure is to be conducted, the device includes a least one window through which the instrumentality for conducting the procedure can be extended. In most instances the instrumentality will be a laser beam. Thus, in the exemplary embodiment shown there are four pairs 44 of slits or apertures that are provided at equidistantly spaced locations around the periphery of the wall 26 of the device 20. These pairs are located at the 1:30, 4:30, 7:30 and 10:30 positions of a clock face, as shown in FIG. 2. Each pair of slits 44 includes two slits 44A and 44B. Each slit is of the same size and shape. In the exemplary embodiment shown each of the slits 44A and 44B is approximately 4.5 mm long and 1 mm wide. The slits 44A and 44B of each pair 44 are separated from each other by approximately 1.2 mm and preferably by 1.5 mm. The slits start approximately 0.5 mm from the surgical limbus.

Use of the device 20 is as follows. The device is placed on the eye 10 so that the upper ring 32, with its opening 30 engages the sclera 12 closely adjacent and surrounding the cornea 11. At the same time the lower ring is located so that its opening 28 engages the sclera 12 remote from the cornea. Thus, the upper ring will engage a circular peripheral portion of the eye along what will be referred to as a first engagement line, while the lower ring will engage a circular peripheral portion of the eye along what will be referred to as a second engagement line. The device 20 is now ready to be operated, whereupon the user of the device depresses the top button or cap 42. This action causes the spring to release and drive the piston forward, whereupon the fluid within the syringe 40 passes through the tube 38 and inflates the two rings 32 and 34. Since each ring encircles a portion of the eye, each ring acts somewhat like an inflatable cuff to apply pressure to the eye (compress the eye) along its respective line of engagement. The application of pressure along the lines of engagement effectively reduces bleeding at the surface of the eye. Accordingly, the surgery can be conducted in a relatively blood free field. In order to accomplish the desired procedure, e.g., laser surgery to correct presbyopia, the laser beam can be introduced through any of the slits 44A or 44B, while the inflated rings maintain the compression on the eye. After the surgery is completed the rings 32 and 34 are deflated, thereby releasing the pressure/compression on the eye and enabling the device 20 to be removed.

It should be pointed out at this juncture that the use of inflatable rings as described above is not the only way that compression can be applied to the underlying surfaces of the eye in accordance with this invention. Thus, it is contemplated that devices constructed in accordance with this invention may make use of a vacuum or suction to effect the application of pressure to spaced apart peripheral portions of the eye, while enabling a laser or other instrument to pass through some aperture or window in the device to operate on the surface of the eye between the spaced apart peripheral portions of the eye. To that end an alternative device of this invention may comprise an peripheral frusto-conical or cylindrical wall having an upper ring surrounding a top opening and a lower ring surrounding a bottom opening. Unlike the embodiment 20 described above in this alternative embodiment the two rings are not an inflatable members. Instead each is preferably formed of a resilient material that is adapted to engage the eye and apply pressure to it along the line of engagement by the application of a vacuum to the space between the rings. In this alternative embodiment each of the windows, e.g., each pairs of slits, is surrounded by a peripheral wall preferably formed of the same material as the upper and lower rings since it will also engage the surface of the eye. These peripheral walls serve to isolate the space between the upper and lower rings from the slits, thereby enabling the vacuum to be maintained. The application of the vacuum to the space between the upper and lower rings is effected by an alternative spring biased syringe. In particular, the syringe is arranged to create a vacuum in the tube 38 when the syringe is actuated, whereupon air from the space between the two rings will be drawn into the syringe, thereby creating a vacuum in the space between the rings. This vacuum will tend to pull the rings into engagement with the eye, whereupon the rings will apply compression to the eye in a similar manner as described above. Since each pair of slit is surround by resilient peripheral wall, the vacuum is maintained in the space between the rings, notwithstanding the fact that the slits are open to enable the laser beam or any desired surgical instrument to be extended through them.

As will be appreciated by those skilled in the art, the device of this invention represents a major new development for ocular surgery, since it speeds up the surgery while reducing complications related to bleeding in the operative field.

Without further elaboration the foregoing will so fully illustrate my invention that others may, by applying current or future knowledge, adopt the same for use under various conditions of service.

I claim:

1. A device for applying external compression to the eye of a living being to reduce bleeding when operating on the surface of the eye, said device comprising a peripheral wall having an open upper end and an open lower end, a first ring member located adjacent said upper end of said wall and operative when actuated for applying pressure to a first portion of the eye closely adjacent and surrounding the cornea, a second ring member located adjacent said lower end of said wall operative when actuated for applying pressure to a second portion of the eye remote from the cornea, fluid pressure means for causing at least portions of said rings to apply pressure to said first and second portions of the eye, said wall including at least one window to enable a laser beam or other instrumentality to be extended therethrough to operate on the surface of the eye between the portions of the eye engaged by said ring members.

2. The device of claim 1 wherein each of said ring members is an inflatable ring arranged to be inflated with an inflation fluid from an external source.

3. The device of claim 1 wherein said external source comprises a spring biased syringe to provide inflation fluid under pressure into said inflatable rings.

4. The device of claim 3 wherein said inflatable rings are in fluid communication with each other.

5. The device of claim 1 wherein said at least one window comprises at least one slit.

6. The device of claim 5 wherein said at least one slit is generally linear and approximately 4.5 mm long and approximately 1 mm wide.

7. The device of claim 5 wherein said at least one window comprises plural pairs of slits, each of said pair of slits comprising two slits separated from each other by 1–2 mm, and wherein each of said slits is generally linear and approximately 4.5 mm long and 1 mm wide.

8. The device of claim 7 comprising four pairs of slits, said pairs of slits being equidistantly located about the periphery of said peripheral wall.

9. A method of applying external compression to the eye of a living being to reduce bleeding when operating on the surface of the eye, said method comprising:
   a) providing device comprising wall having a window therein, a first ring member and a second ring member; and
   b) causing said first ring member to apply pressure to a first peripheral portion of the eye closely adjacent and surrounding the cornea and causing said second ring member to apply pressure to a second peripheral portion of the eye remote from the cornea, whereupon a laser beam or other instrumentality can be extended through said window to operate on the surface of the eye between the first and second peripheral portions of the eye.

10. The method of claim 9 additionally comprising:
c) extending a laser beam or other instrumentality through said window to operate on the surface of the eye between the first and second peripheral portions of the eye.

11. The method of claim 9 wherein said actuatable rings are actuated by fluid pressure and wherein said method comprises applying fluid pressure to said rings to effect their actuation.

12. The method of claim 11 wherein each of said rings is inflatable and wherein said method comprises:
c) inflating said rings.

* * * * *